United States Patent [19]

Hamilton et al.

[11] Patent Number: 5,135,914
[45] Date of Patent: Aug. 4, 1992

[54] SUBSTITUTED DERIVATIVES OF 3-AMINO-2-HYDROXYPROPIONIC ACID AS INHIBITORS OF RENIN

[75] Inventors: Harriet W. Hamilton; William C. Patt, both of Chelsea, Mich.

[73] Assignee: Warner-Lambert Company, Morris Plains, N.J.

[21] Appl. No.: 197,547

[22] Filed: May 23, 1988

[51] Int. Cl.$^5$ .................. A61K 31/415; C07D 233/64
[52] U.S. Cl. ...................................... 514/19; 548/344
[58] Field of Search .................. 514/19, 385; 544/159; 548/344

[56] References Cited

U.S. PATENT DOCUMENTS 4,814,342 3/1989 Hoover .............................. 514/385

OTHER PUBLICATIONS

Bolis et al, Renin Inhibitors, J Med Chem 1987, 30 1729-1737.
Haber et al, Renin Inhibitors, J Cardio Pharm 1987, 10 (Supp 7) 554-558.
Plattner et al, Renin Inhibitors, J Med Chem 1988, 31 2277-2288.
Denkewalker et al, Progress in Drug Research, vol. 10 1966 510-512.
Medicinal Chemistry, A. Burger 1960 565-601.
Boger et al., Hypertension vol. 15, No. 6, Part 2, pp. 835-840 (Jun. 1990).
Webb et al., J. Cardiovascular Pharm., vol. 10 (Suppl. 7), pp. 569-574 (1987).
Zhou et al., Clin. Pharm. 2nd Therapeutics, vol. 47, p. 141 (1990).
van der Meiracker, British Med. J., vol. 301, pp. 205-210 (Jul. 1990).

*Primary Examiner*—Mary C. Lee
*Assistant Examiner*—M. S. H. Gabilan
*Attorney, Agent, or Firm*—Francis J. Tinney

[57] ABSTRACT

Novel substituted derivatives of 3-amino-2-hydroxypropionic acid are described, as well as methods for the preparation and pharmaceutical compositions of same, which are useful as renin inhibitors and thus useful in controlling hypertension, hyperaldosteronism and congestive heart failure as well as diagnostic agents.

6 Claims, No Drawings

SUBSTITUTED DERIVATIVES OF 3-AMINO-2-HYDROXYPROPIONIC ACID AS INHIBITORS OF RENIN

BACKGROUND OF THE INVENTION

The present invention relates to novel substituted derivatives of 3-amino-2-hydroxypropionic acid useful as pharmaceutical agents, to methods for their production, to pharmaceutical compositions which include these compounds and a pharmaceutically acceptable carrier, and to pharmaceutical methods of treatment as well as the use of these agents as diagnostic tools. More particularly, the novel compounds of the present invention inhibit the enzyme renin thus controlling hypertension, hyperaldosteronism and congestive heart failure in mammals.

Renin is a natural enzyme which is released into the blood stream from the kidney. It cleaves its natural substrate, angiotensinogen, releasing a decapeptide, angiotensin I. This in turn is cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renin have been sought as agents for control of hypertension and hyperaldosteronism.

U.S. Pat. No. 4,656,269 discloses certain renin-inhibiting peptides of the formula

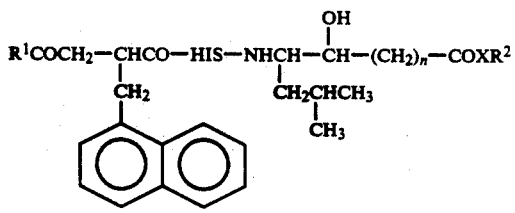

wherein $R^1$ represents a monoalkylamino group having one to three carbon atoms, a dialkylamino group having two to six carbon atoms, or

in which Y represents a chemical bond, an oxygen atom or a methylene group, His represents an L-histidyl group, n represents zero or 1, X represents an oxygen atom or —NH—, $R^2$ represents a straight or branched alkyl group having one to seven carbon atoms.

European Patent Application 0.216,539 discloses reinin-inhibiting peptides of the formula

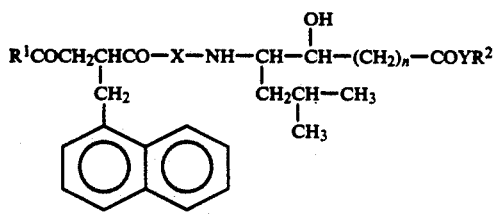

wherein $R^1$ represents

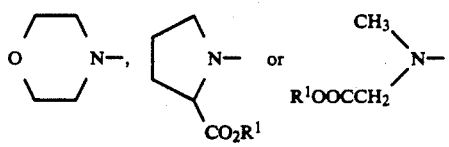

in which $R^1$ represents a lower alkyl group, X represents an amino acid residual group selected from glycine, alanine, $\beta$-alanine, valine, leucine, phenylalanine, tryptophane and serine, n is zero or 1, Y represents —O—, or —NH—, and $R^2$ represents a straight- or branched-chain alkyl group having one to seven carbon atoms. European Patent Application 0,200,406 disclosed a renin-inhibiting peptide of the formula

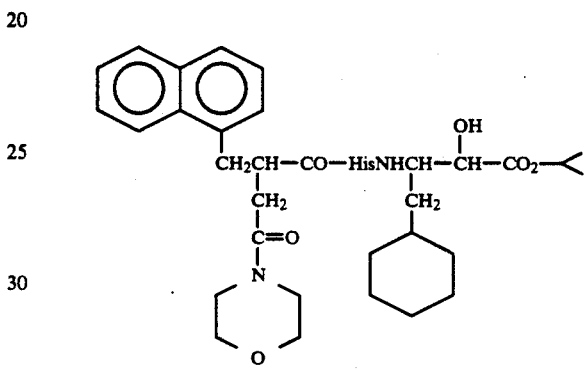

SUMMARY OF THE INVENTION

Accordingly, the present invention relates to novel compounds having the formula I $$A-CH_2-CH-\overset{O}{\overset{\|}{C}}-NH-CH-\overset{O}{\overset{\|}{C}}-NH-CH-\overset{OH}{\overset{|}{CH}}-\overset{O}{\overset{\|}{C}}-E \quad I$$
$$\phantom{A-CH_2-}\overset{|}{G}\phantom{-C-NH-}\overset{|}{J}\phantom{-C-NH-CH-}\overset{|}{D}$$

or a pharmaceutically acceptable acid addition salt thereof, wherein A is naphthyl, phenyl, or phenyl substituted with alkyl of from one to four carbon atoms, or alkoxy of from one to four carbon atoms, G is naphthylmethyl,

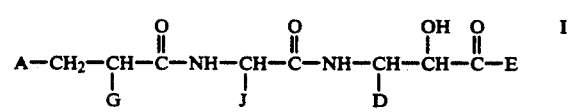

$$C_6H_5-\overset{O}{\overset{\|}{C}}CH_2-,$$

or $R,R_1NSO_2NH—$, wherein R and $R_1$ are each independently hydrogen, alkyl of from one to six carbon atoms or R and $R_1$ taken together form a ring of from five to seven atoms which may be interrupted by a heteroatom comprising O, S or $R_2N—$, wherein $R_2$ is hydrogen or alkyl of from one to three carbon atoms; J is

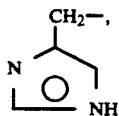

$R_3O_2C-$, wherein $R_3$ is alkyl of from one to five carbon atoms, or $R_4NH(CH_2)_n-$, wherein n is an integer of from four to six and $R_4$ is

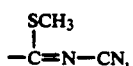

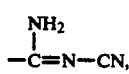

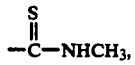

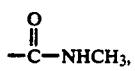

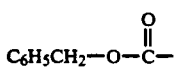

or

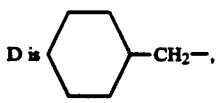

or $(CH_3)_2CHCH_2-$; and E is $R_5O-$, wherein $R_5$ is alkyl of from one to five carbon atoms or $R_6CH_2-$, wherein $R_6$ is phenyl, 2, 3, or 4-pyridinyl, $R_5NH-$, wherein $R_5$ is as defined above, or $R_7R_8N-$, wherein $R_7$ and $R_8$ form a cyclic ring of four to seven carbon atoms which may be interrupted by another heteroatom comprising O, S, or $R_2N-$, wherein $R_2$ is as defined above, with the proviso that when D is as defined above A id not naphthyl, G is not

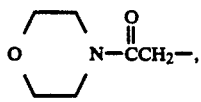

and J is not

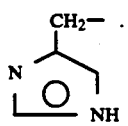

Other embodiments of the present invention include pharmaceutical compositions comprising an effective amount of a compound of formula I in admixture with a pharmaceutically acceptable carrier, and a method for treating renin-associated hypertension in a patient suffering therefrom comprising administering to said patient the above pharmaceutical composition in unit dosage form.

Further embodiments of the present invention include a pharmaceutical composition comprising an effective amount of a compound of formula I above in admixture with a pharmaceutically acceptable carrier, and a method for treating hyperaldosteronism in a patient suffering therefrom comprising administering to said patient the above pharmaceutical composition in unit dosage form.

A still further embodiment of the present invention also includes a pharmaceutical composition comprising an effective amount of a compound of formula I in admixture with a pharmaceutically acceptable carrier, and a method for treating congestive heart failure in a patient suffering therefrom comprising administering to said patient the above pharmaceutical composition in unit dosage form.

A still further embodiment of the present invention also includes the use of compounds of formula I above as diagnostic tools for the identification of cases of hypertension due to renin excess.

Finally, the present invention is directed to methods for production of a compound of formula I.

DETAILED DESCRIPTION OF THE INVENTION

In the compounds of formula I, the term "alkyl" means a straight or branched hydrocarbon radical having from one to six carbon atoms and includes, for example, methyl, ethyl, n-propyl, isopropyl, n-butyl, isobutyl, tertiary-butyl, n-pentyl, n-hexyl, and the like.

"Alkoxy" is 0-alkyl in which alkyl is as defined above.

The compounds of formula I are capable of further forming pharmaceutically acceptable acid addition salts. Both of these forms are within the scope of the present invention. Pharmaceutically acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al., "Pharmaceutical Salts," *Journal of Pharmaceutical Science*, 66, pp. 1-19 (1977)). The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated as well as solvated forms, including hydrated forms. In general, the solvated forms, including hydrated forms are equivalent to unsolvated forms and are intended to be encompassed within the scope of the present invention.

The compounds of the present invention possess one or more chiral centers and each center may exist in the R(D) or S(L) configuration. The present invention includes all enantiomeric and epimeric forms as well as the appropriate mixtures thereof.

A preferred compound of formula I is one wherein A is 1-naphthyl, phenyl, or 4-methoxyphenyl; G is 1-naphthylmethyl,

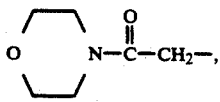

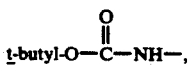

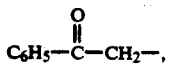

or R,R$_1$NSO$_2$NH—, wherein R and R$_1$ are each independently hydrogen, alkyl of from one to six carbon atoms or R and R$_1$ taken together form a ring of from five to seven atoms which may be interrupted by a heteroatom comprising O, S, or R$_2$N—, wherein R$_2$ is hydrogen or alkyl of from one to three carbon atoms; J is

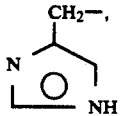

R$_3$O$_2$C—, wherein R$_3$ is alkyl of from one to five carbon atoms, or R$_4$NH(CH$_2$)$_n$—, wherein n is an integer of from four to six and R$_4$ is

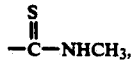

or

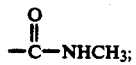

D is 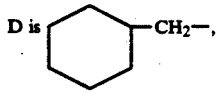

or

(CH$_3$)$_2$CHCH$_2$—;

and E is R$_5$O—, wherein R$_5$ is alkyl of from one to five carbon atoms.

Another preferred embodiment is a compound of formula I wherein G is 1-naphthylmethyl,

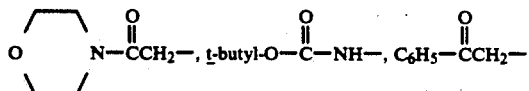

or (CH$_3$)$_2$NSO$_2$NH—; J is

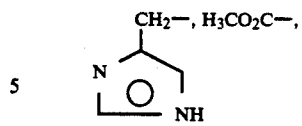

or R$_4$NH(CH$_2$)$_4$—, wherein R$_4$ is

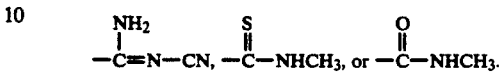

Particularly valuable are:

[R-(R*,S*)]-N-[(Dimethylamino)sulfonyl]-L-phenylalanyl-N-[1-[1-hydroxy-2-(1-methylethoxy-2-oxoethyl]-3-methylbutyl]-L-histidinamide;

[R-(R*,S*) ]-N-[N-[(Dimethylamino)sulfonyl]-L-phenylalanyl]-3-[[1-[1-hydroxy-2-(1-methylethoxy)-2-oxoethyl]-3-methylbutyl]amino]-3-oxo-L-alanine, methyl ester;

[R-(R*,S*)]-N-[(Dimethylamino)sulfonyl]-L-phenylalanyl-N-[1-[1-hydroxy-2-(1-methylethoxy)-2-oxoethyl]-3-methylbutyl]-N$^6$-[(methylamino)thioxomethyl]-L-lysinamide;

[R-(R*,S*)]-N-[(Dimethylamino)sulfonyl]-L-phenylalanyl-N$^6$-[amino(cyanoimino)methyl]-N-[1-[1-hydroxy-2-(1-methylethoxy)-2-oxoethyl]-3-methylbutyl]-L-lysinamide;

[R-(R*,S*)]-N-[(1,1-Dimethylethoxy)carbonyl]-O-methyl-L-tyrosyl-N-[1-[1-hydroxy-2-(1-methylethoxy)-2-oxoethyl]-3-methylbutyl]-L-histidinamide;

[R-(R*,S*)]-N-[(1,1-Dimethylethoxy)carbonyl]-O-methyl-L-tyrosyl]-3-[[1-[1-hydroxy-2-(1-methylethoxy)-2-oxoethyl]-3-methylbutyl]amino]-3-oxo-L-alanine, methyl ester;

[R-(R*,S*)]-N-[(1,1-Dimethylethoxy)carbonyl]-O-methyl-L-tyrosyl]-N-[1-[1-hydroxy-2-(1-methylethoxy)-2-oxoethyl]-3-methylbutyl]-N$^6$-[(methylamino)thioxomethyl]-L-lysinamide;

[R-(R*,S*)]-N-[(1,1-Dimethylethoxy)carbonyl]-O-methyl-L-tyrosyl]-N$^6$-[amino(cyanoimino)methyl]-N-[1-hydroxy-2-(1-methylethoxy)-2-oxoethyl]-3-methylbutyl]-L-lysinamide;

[R-(R*,S*)]-N-[(Dimethylamino)sulfonyl]-L-phenylalanyl-N-[1-(cyclohexylmethyl)-2-hydroxy-3-(1-methylethoxy)-3-oxopropyl]-L-histidinamide;

[R-(R*,S*)]-N-[N-[(Dimethylamino)sulfonyl]-L-phenylalanyl-N-[1-(cyclohexylmethyl)-2-hydroxy-3-(1-methylethoxy)-3-oxopropyl]-3-oxo-L-alanine, methyl ester;

[R-(R*,S*)]-N-[(Dimethylamino)sulfonyl]-L-phenylalanyl-N-[1-(cyclohexylmethyl)-2-hydroxy-3-(1-methylethoxy)-3oxopropyl]-N$^6$-[(methylamino)thioxomethyl]-L-lysinamide;

[R-(R*,S*)]-N-[(Dimethylamino)sulfonyl]-L-phenylalanyl-N$^6$-[amino(cyanoimino)methyl]-N-[1-(cyclohexylmethyl)-2-hydroxy-3-(1-methylethoxy)-3-oxopropyl]-L-lysinamide;

[R-(R*,S*)]-N-[(1,1-Dimethylethoxy)carbonyl]-O-methyl-L-tyrosyl-N-[1-(cyclohexylmethyl)-2-hydroxy-3-(1-methylethoxy)-3-oxopropyl]-L-histidinamide;

[R-(R*,S*) ]-N-[N-[(1,1-Dimethylethoxy)carbonyl]-O-methyl-L-tyrosyl]-3-[[1-(cyclohexylmethyl)-2-hydroxy-3-(1-methylethoxy)-3-oxopropyl]amino]-3-oxo-L-alanine, methyl ester;

[R-(R*,S*)]-N-[(1,1-Dimethylethoxy)carbonyl]-O-methyl-L-tyrosyl]-N-[1-(cyclohexylmethyl)-2-hydroxy-3-

(1-methylethoxy)-3-oxopropyl]-N⁶-[(methylamino)-thioxomethyl]-L-lysinamide;

R-(R*,S*)]-N-[(1,1-Dimethylethoxy)carbonyl]-O-methyl-L-tyrosyl]-N⁶-[amino(cyanoimino)methyl]-N-[1-(cyclohexylmethyl)-2-hydroxy-3-(1-methylethoxy)-3-oxopropyl]-L-lysinamide;

N-[(1,1-Dimethylethoxy)carbonyl]-L-phenylalanyl-N-[1-[1-hydroxy-2-(1-methylethoxy)-2-oxoethyl]-3-methylbutyl-L-histidinamide (hydroxy center is RS; all other centers are S);

2-Hydroxy-3-[[3-(1H-imidazol-4-yl)-2-[[3-(1-naphthalenyl)-2-(1-naphthalenylmethyl)-1-oxopropyl]amino]-1-oxopropyl]amino]-5-methylhexanoic acid, 1-methylethyl ester, acetate (1:1) (salt) (hydroxy center RS; other centers S);

[2R-[2R*,3S*(S*)]]-2-Hydroxy-3-[[-3-(1H-imidazol-4-yl)-2-[[3-(1-naphthalenyl)-2-(1-naphthalenylmethyl)-1-oxopropyl]amino]-1-oxopropyl]amino]-5-methylhexanoic acid, 1-methylethyl ester;

[2R*,3S*(S*)]]-3-[[2-[[3-Benzoyl-2-(1-naphthalenylmethyl)-1-oxopropyl]amino]-3(1H-imidazol-4-yl)-1-oxopropyl]amino]-2-hydroxy-5-methylhexanoic acid, 1-methylethyl ester;

[2R-[2R*,3S*(S*)]]-2-Hydroxy-5-methyl-3-[[6-[[(methylamino)thioxomethyl]amino]-2-[[3-(1-naphthalenyl)-2-(1-naphthalenylmethyl)-1-oxopropyl]amino]-1-oxohexyl]amino]hexanoic acid, 1-methylethyl ester;

[2R-[2R*,3S*(S*)]]-2-Hydroxy-5-methyl-3-[[6-[[(methylamino)thioxomethyl]amino]-2-[[4-(4-morpholinyl)-2-(1-naphthalenylmethyl)-1,4-dioxobutyl]amino]-1-oxohexyl]amino]hexanoic acid, 1-methylethyl ester;

[2S-[2R*,3R*(R*)]]-2-Hydroxy-5-methyl-3-[[6-[[(methylamino)thioxomethyl]amino]-2-[[4-(4-morpholinyl)-2-(1-naphthalenylmethyl)-1,4-dioxobutyl]amino]-1-oxohexyl]amino]hexanoic acid, 1-methylethyl ester;

[2R-[2R*,3S*(S*)]]-2-Hydroxy-5-methyl-3-[[2-[[4-(4-morpholinyl)-2-(1-naphthalenylmethyl)-1,4-dioxobutyl]amino]-1-oxo-(phenylmethoxy)carbonyl]amino]hexyl]amino]hexanoic acid, 1-methylethyl ester;

[2R-[2R*,3S*(S*)]]-2-Hydroxy-5-methyl-3-[[2-[[3-(1-naphthalenyl-2-(1-naphthalenylmethyl)-1-oxopropyl]amino]-1-oxo-6-[[(phenylmethoxy)carbonyl]amino]hexyl]amino]hexanoic acid, 1-methylethyl ester;

or a pharmaceutically acceptable acid addition salt thereof.

The compounds of the present invention are valuable because of their ability to inhibit renin in an in vitro assay. Activity is determined by a standard radioimmunoassay for angiotensin I. In the assay, the enzyme renin, incubated for two hours at 37° in the presence of a substrate, angiotensinogen, generates the product angiotensin I. Test compounds are added to the incubation mixture. Relative activity is reported as the IC₅₀, which is the molar concentration of test compound causing a 50% inhibition of the renin activity. The data in Table 1 shows the ability of representative compounds of the present invention to inhibit renin.

The in vitro test employed is more fully described in "Methods in Enzymatic Analysis", Bergmeyer, J., and Grass, N., eds., 3rd edition Weinheim: Verlag Chemie, pp. 251-258 (1984).

As can be seen from the above table, the compounds of the present invention have a significant effect on the activity of renin and thus are useful for the treatment of hypertension, congestive heart failure, and hyperaldosteronism. They are also useful as diagnostic tools for determining the presence of renin-associated hypertension or hyperaldosteronism.

TABLE 1

Biological Activity of Compounds of Formula I

| Example Number | Compound | IC₅₀(M) |
|---|---|---|
| 1 | N-[(1,1-dimethylethoxy)carbonyl]-L-phenylalanyl-N-[1-[1-hydroxy-2-(1-methylethoxy)-2-oxoethyl]-3-methylbutyl-L-histidinamide (hydroxy center is RS; all other centers are S) | 1 × 10⁻⁶ |
| 1b | [2R-[2R*,3S*(S*)]]-2-hydroxy-3-[[-3-(1H-imidazol-4-yl)-2-[[3-(1-naphthalenyl)-2-(1-naphthalenylmethyl)-1-oxopropyl]amino]-1-oxopropyl]amino]-5-methylhexanoic acid, 1-methylethyl ester | 1.4 × 10⁻⁷ |

The process of preparing compounds of the present invention is described generally as follows.

A compound of formula I

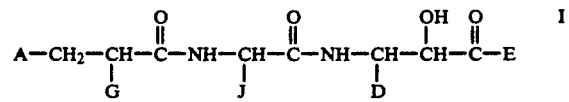

or a pharmaceutically acceptable acid addition salt thereof, wherein A is naphthyl, phenyl, or phenyl substituted with alkyl of from one to four carbon atoms, or alkoxy of from one to four carbon atoms; G is naphthylmethyl,

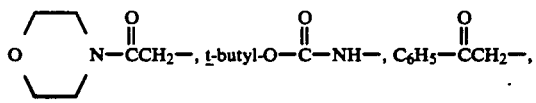

or R,R₁NSO₂NH—, wherein R and R₁ are each independently hydrogen, alkyl of from one to six carbon atoms or R and R₁ taken together form a ring of from five to seven atoms which may be interrupted by a heteroatom comprising O, S, or R₂N—, wherein R₂ is hydrogen or alkyl of from one to three carbon atoms; J is

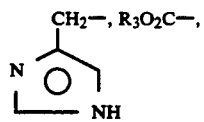

wherein R₃ is alkyl of from one to five carbon atoms, or R₄NH(CH₂)ₙ—, wherein n is an integer of from four to six and R₄ is

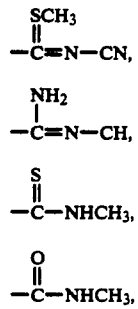

-continued

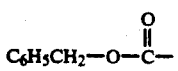

or

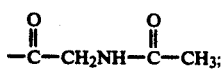

D is 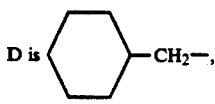

or

 and E and E is $R_5O$, wherein $R_5$ is alkyl of from one to five carbon atoms or $R_6CH_2$—, wherein $R_6$ is phenyl, 2, 3, or 4-pyridinyl, $R_5NH$—, wherein $R_5$ is as defined above, or $R_7R_8N$—, wherein $R_7$ and $R_8$ form a cyclic ring of four to seven carbon atoms which may be interrupted by another heteroatom comprising O, S, or $R_2N$—, wherein $R_2$ is as defined above with the proviso that when D is as defined above A is not naphthyl; G is not

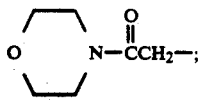

and J is not

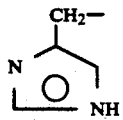

is prepared by reacting a compound of formula II

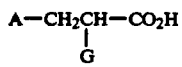     II wherein A and G are as defined above with a compound of formula III

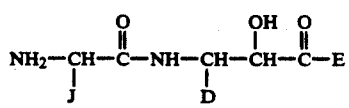     III wherein J, D and E are as defined above with a coupling reagent such as, for example, 1,3-dicyclohexylcarbodiimide (DCC), bis(2-oxo-3-oxazolidinyl)phosphinic chloride (BOP-Cl) and the like, and if desired 1-hydroxybenzotriazole (HOBT) in the presence of an inert solvent such as, for example, methylene chloride, dimethylformamide, dioxane, tetrahydrofuran and the like at about −5° C. to about 25° C. Preferably the reaction is carried out using DCC and HOBT in dimethylformamide at about 0° C. to give a compound of formula I.

A compound of formula II is either known or capable of being prepared by methods known in the art.

A compound of formula III is prepared by reacting a compound of formula IV

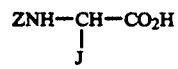     IV wherein Z is benzyloxycarbonyl and J is as defined above with a compound of formula V

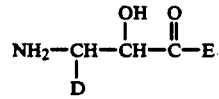     V wherein D and E are as defined above With a coupling reagent such as, for example, DCC, BOP-Cl and the like and if desired HOBT in the presence of an inert solvent such as, for example, methylene chloride, dimethylformamide, dioxane, tetrahydrofuran and the like at about −5° C. to about 25° C. Preferably the reaction is carried out using DCC and HOBT in dimethylformamide at about 0° C. to give a compound of formula VI

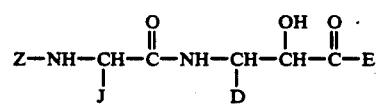     VI wherein Z, J, D and E are as defined above.

A compound of formula VI is reacted with an acid such as, for example, hydrogen bromide in acetic acid and the like or alternatively hydrogenated in the presence of a catalyst, such as, for example, palladium on carbon and the like in a polar inert solvent such as, for example, methanol and the like at about 0° C. to about 25° C. Preferably the reaction is carried out by hydrogenating a compound of formula VI in the presence of palladium on carbon in methanol at about 25° C. to afford a compound of formula III.

A compound of formula IV is either known or capable of being prepared by methods known in the art.

A compound of formula V is prepared from a compound of formula VII

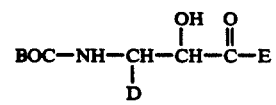     VII wherein BOC is tertiary butoxycarbonyl and D and E are as defined above by reaction with an acid such as, for example, trifluoroacetic acid, hydrochloric acid and the like either neat or in the presence of an inert solvent such as, for example, methylene chloride, dioxane, diethyl ether and the like at about 0° to about 25° C. Preferably the reaction is carried out using hydrochloric acid in methylene chloride at about 0° C. to afford a compound of formula V.

A compound of formula VII wherein D is

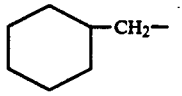

and BOC and E are as defined above is prepared from a compound of formula VIII

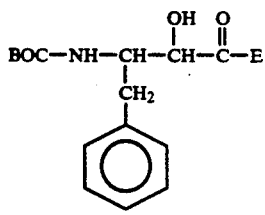

wherein BOC and E are as defined above by hydrogenation in the presence of a catalyst such as, for example, rhodium on carbon and the like in a polar inert solvent such as, for example, isopropanol and the like at about 0° C. to about 25° C. Preferably the reaction is carried out in the presence of rhodium on carbon in isopropanol at about 25° C. to afford a compound of formula VII, wherein D is

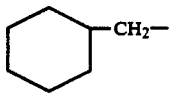

and BOC and E are defined above.

A compound of formula VIII wherein E is $R_5O-$ and $R_5$ and BOC are as defined above is prepared from a compound of formula IX

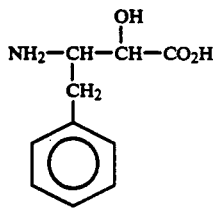

by reaction with a compound of formula

<p style="text-align:center">$R_5OH$</p> wherein $R_5$ is as defined above in the presence of an acid such as, for example, hydrochloric acid and the like and an inert solvent such as, for example, toluene and the like and if desired in the presence of 3A molecular sieves at about 25° C. to about the reflux temperature of the inert solvent. Preferably the reaction is carried out in the presence of hydrochloric acid, toluene and 3A molecular sieves at reflux. The resulting intermediate compound is further reacted with a base such as, for example, triethylamine and the like and a tertiary butoxycarbonylation reagent such as, for example, di-tertiary butyldicarbonate and the like in an inert solvent such as, for example, aqueous dioxane at about 0° to about 25° C. Preferably the reaction is carried out in the presence of triethylamine, di-tertiary butyldicarbonate and aqueous dioxane at about 25° C. to afford a compound of formula VIII wherein E is $R_5O-$ and $R_5$ and BOC are as defined above.

A compound of formula VIII wherein E is $R_5NH-$ or $R_7R_8N-$ and $R_5$, $R_7$, $R_8$ and BOC are as defined above is prepared by reacting a compound of formula IX with a base such as, for example, triethylamine and the like and a tertiary butoxycarbonylation reagent such as, for example, di-tertiary butyldicarbonate and the like in an inert solvent such as, for example, aqueous dioxane at about 0° C. to about 25° C. Preferably the reaction is carried out in the presence of triethylamine, di-tertiary butyldicarbonate and aqueous dioxane at about 25° C. to afford a compound of formula X

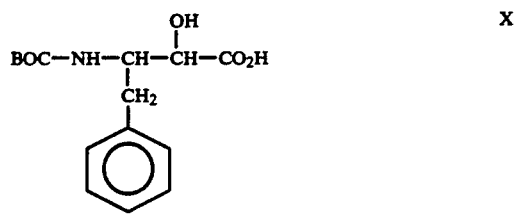

wherein BOC is as defined above.

The resulting compound of formula X is further reacted with a compound of $R_5NH_2$ or wherein $R_5$, $R_7$ and $R_8$ are as defined above in the presence of a coupling reagent such as, for example, DCC, BOP-Cl and the like and if desired HOBT in the presence of an inert solvent such as, for example, methylene chloride, dimethylformamide, dioxane, tetrahydrofuran and the like at about $-5°$ C. to about 25° C. Preferably the reaction is carried out using DCC and HOB in dimethylformamide at about 0° C. to afford a compound of formula VIII wherein E is $R_5NH-$ or $R_7R_8N-$ and $R_5$, $R_7$, $R_8$ and BOC are as defined above.

A compound of formula IX is prepared from the known

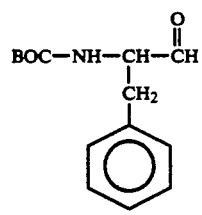

wherein BOC is as defined above using the methodology described by Johnson, R, *Journal of Medicinal Chemistry*, 25, pp. 605–610 (1982).

A compound of formula VII wherein D is $(CH_3)_2CHCH_2-$ and BOC and E are as defined above is prepared by methods known in the art, especially using the methodology described by Rich, D. H., et al., *Journal of Organic Chemistry*, 45, pp. 2288–2290 (1980).

Additionally, if desired a compound of formula VII

wherein * indicates an asymmetric carbon atom and BOC, D, and E are as defined above may be separated into optically pure derivatives, for example, (2S,3R), (2R,3R), (2S,3S) and (2R,3S) using the methodology described by Rich, D. H., et al., *Journal of Organic Chemistry*, 45, pp. 2288-2290 (1980).

Alternatively, a compound of formula I is prepared by reacting a compound of formula XI

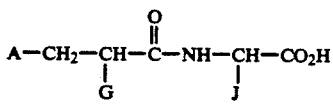

XI wherein A, G and J are as defined above with a compound of formula V in the presence of a coupling reagent such as, for example, DCC, BOP—Cl and the like and if desired HOBT in the presence of an inert solvent such as, for example, methylene chloride, dimethylformamide, dioxane, tetrahydrofuran and the like at about −5° C. to about 25° C. Preferably the reaction is carried out using DCC and HOBT in dimethylformamide at about 0° C. to afford a compound of formula I.

A compound of formula XI wherein A, G and J are as defined above is prepared by reacting a compound of formula II with a compound of formula XII

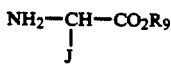

XII wherein $R_9$ is alkyl or form one to five carbon atoms and J is as defined above in the presence of a coupling reagent such as, for example, DCC, BOP-Cl and the like and if desired HOBT in the presence of an inert solvent such as, for example, methylene chloride, dimethylformamide, dioxane, tetrahydrofuran and the like at about −5° C. to about 25° C. Preferably the reaction is carried out using DCC and HOBT in dimethylformamide at about 0° C. to afford a compound of formula XIII

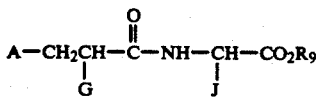

XIII wherein A, G, J and $R_9$ are as defined above.

A compound of formula XIII, wherein A, G, J and $R_9$ are as defined above is reacted with a base such as, for example, sodium hydroxide, potassium hydroxide and the like in the presence of an aqueous alcohol such as, for example, methanol at about 0° C. to about the reflux temperature of the solvent. Preferably the reaction is carried out with sodium hydroxide in aqueous methanol at 25° C. to afford a compound of formula XI.

A compound of formula XII is either known or capable of being prepared by methods known in the art.

Preferably a compound of formula Ia

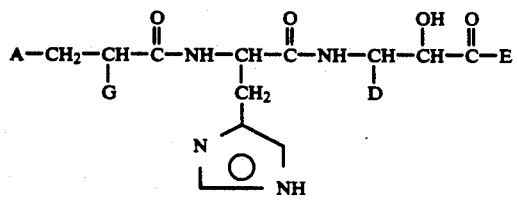

$I_a$ wherein A, G, D and E are as defined above is prepared from a compound of formula XIV

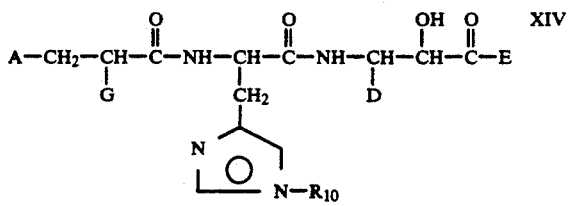

XIV wherein $R_{10}$ is a protecting group and A, G, D and E are as defined above by removal of the protecting group. For example, when $R_{10}$ is triphenylmethyl the reaction is carried out in an aqueous acid such as, for example, aqueous acetic acid and the like at about 25° C. to about 100° C. Preferably the reaction is carried out in aqueous acetic acid at about 80° C. to afford a compound of formula $I_a$.

Preferably a compound of formula $I_b$

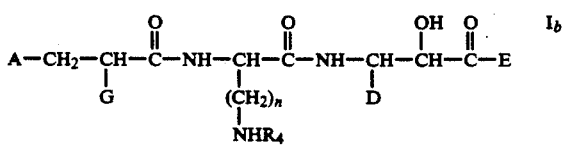

$I_b$ wherein $R_4$ is

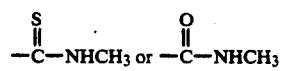

and A, G. D, E and n are as defined above is prepared by reacting a compound of formula XV

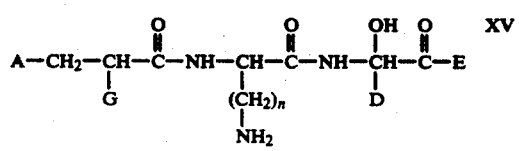

XV wherein A, G, D, E and n are as defined above with a compound of formula

$CH_3—N=C=X$ wherein X is O or S in the presence of an inert solvent such as, for example, chloroform and the like at about 0° to about the reflux temperature of the solvent. Preferably the reaction is carried out in chloroform at about 25° C. to afford a compound of formula $I_b$.

Preferably a compound of formula $I_c$

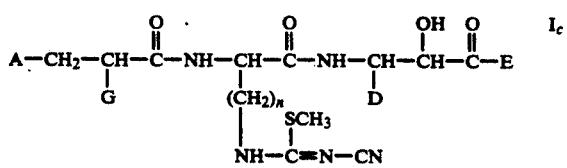

$I_c$ wherein A, G, D, E and n are as defined above is prepared by reacting a compound of formula XV wherein A, G, D, E and n are as defined above with dimethyl-N-cyanodithioiminocarbonate in an inert solvent to afford a compound of formula $I_c$.

Preferably a compound of formula $I_d$

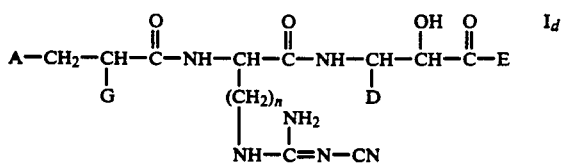

wherein A, G, D, E and n are as defined above is prepared by reacting a compound of formula XV wherein A, G, D, E and n are as defined above with diphenyl cyanocarbonimidate in an inert solvent followed by ammonia to afford a compound of formula $I_d$.

Preferably a compound of formula $I_3$

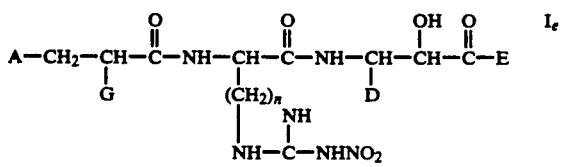

wherein A, G, D, E and n are as defined above is prepared by reacting a compound of formula XV wherein A, G, D, E and n are as defined above with N-nitrocarbaminidothioic acid, methyl ester in an inert solvent to afford a compound of formula $I_e$.

Preferably a compound of formula $I_f$

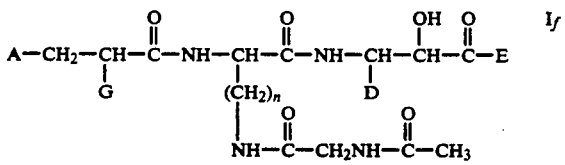

wherein A, G, D, E and n are as defined above is prepared by reacting a compound of formula XV wherein A, G, D, E and n are as defined above with N-acetylglycine with a coupling reagent such as DCC using the same procedure described for preparing a compound of formula I from a compound of formula II and a compound of formula III.

A compound of formula XV is prepared from a compound of formula XVI

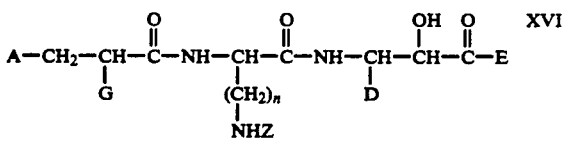

wherein A, G, D, E, n, and Z are as defined above by hydrogenation in the presence of a catalyst such as, for example, palladium on carbon and the like in a polar inert solvent such as, for example, ethanol at about 0° C. to about 25° C. Preferably the reaction is carried out in the presence of palladium on carbon in ethanol at 25° C. to afford a compound of formula XV.

Compounds of formula XIV and XVI are prepared by the general methods previously described for preparing a compound of formula I.

Other coupling methods that can be employed in preparing the compounds of formula I are discussed in "The Peptides. Analysis, Synthesis, Biology," Gross, E., and Meienhofer, J., eds., Academic Press, New York, N.Y., Vol. 1, 1979. Further, other protecting groups that may be employed in the preparation of a compound of formula I, as well as methods for incorporation and removal of these protecting groups are discussed in "The Peptides. Analysis, Synthesis, Biology," Gross, E., and Meienhofer, J., eds., Academic Press, New York, N.Y., Vol. 3, 1981.

The compounds of the present invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can also be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 1 mg to 10 mg according to the particular application and the potency of the active component. The composition can, if desired, also contain other compatible therapeutic agents.

In therapeutic use as agents for treating renin-associated hypertension, hyperaldosteronism, and congestive heart failure or for determining the presence of renin-associated hypertension, the compounds utilized in the pharmaceutical method of this invention are administered at the initial dosage of about 0.1 mg to about 100 mg per kilogram daily. A daily dose range of about 1 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

N-[(1,1-dimethylethoxy)carbonyl]-L-phenylalanyl-N-[1-[1-hydroxy-2-(1-methylethoxy)-2-oxoethyl]-3-methylbutyl-L-histidinamide (hydroxy center is RS; other centers are S)

A solution of 1.3 g (1.6 mmol) of N-[(1,1-dimethylethoxy)carbonyl]-L-phenylalanyl-N-[1-[1-hydroxy-2-(1-methylethoxy)-2-oxoethyl]-3-methylbutyl]-1-(triphenylmethyl)-L-histidinamide (mixture of [1S-[1R*(R*)]] and [1S-[1R*(S*)]]isomers) (Example H) in 15 ml of 80% acetic acid is warmed to 100° C. for five minutes, and evaporated in vacuo. The residue is dissolved in 25 ml of ethyl acetate and washed successively with 25 ml of 1N sodium hydroxide solution and 25 ml of saturated sodium chloride solution. The organic layer is separated, warmed, dried (magnesium sulfate), evaporated in vacuo, and the residue triturated with diethyl ether to afford 0.36 g of the title compound as a white solid; mp 141°–144° C.

EXAMPLE 1a

2-Hydroxy-3-[[3-(1H-imidazol-4-yl)-2-[[3-(1-naphthalenyl)-2-(1-naphthalenylmethyl)-1-oxopropyl]amino]-1-oxopropyl]amino]-5-methylhexanoic acid, 1-methylethyl ester, acetate (1:1) (salt) (hydroxy center is RS; other centers are S)

In a process analogous to Example 1 by substituting 2-hydroxy-5-methyl-3-[[2-[[3-(1-naphthalenyl)-2-(1-naphthalenylmethyl)-3-oxopropyl]amino]-1-oxo-3-[1-(triphenylmethyl)-1H-imidazol-4-yl]propyl]amino]hexanoic acid, 1-methylethyl ester (mixture of [2R-[2R*,3S*(S*)]] and [2S-[2R*,3R*(R*)]-isomers) (Example I) for N-[(1,1-dimethylethoxy)carbonyl]-L-phenylalanyl-N[1-[1-hydroxy-2-(1-methylethoxy)-2-oxoethyl]-3-methylbutyl]-1-(triphenylmethyl)-L-histidinamide (mixture of [1S-[1R*(R*)]] and [1S-[1R*(S*)]]isomers) one obtains the title compound; mp 65°–73° C.

EXAMPLE 1b

[2R-[2R*,3S*(S*)]]-2-hydroxy-3-[[-3-(1H-imidazol-4-yl)-2-[[3-(1-naphthalenyl)-2-(1-naphthalenylmethyl)-1-oxopropyl]amino]-1-oxopropyl]amino]-5-methylhexanoic acid, 1-methylethyl ester In a process analogous to Example 1 by substituting [2R-[2R*,3S*(S*)]]-2-hydroxy-5-methyl-3-[[2-[[3-(1-naphthalenyl)-2-(1-naphthalenylmethyl)-3-oxopropyl]amino]-1-oxo-3-[1-(triphenylmethyl)-1H-imidazol-4-yl]propyl]amino]hexanoic acid, 1-methylethyl ester (Example J) for N-[(1,1-dimethylethoxy)carbonyl]-L-phenylalanyl-N-[1-[1-hydroxy-2-(1-methylethoxy)-2-oxoethyl]-3-methylbutyl]-1-(triphenylmethyl)-L-histidinamide (mixture of [1S-[1R*(R*)]] and [1S-[1R*(S*)]]isomers) one obtains the title compound; mp 93°–98° C.

EXAMPLE 1c

[2R-[2R*,3S*(S*)]]-3-[[2-[[3-benzoyl-2-(1-naphthalenylmethyl)-1-oxopropyl]amino]-3-(1H-imidazol-4-yl)-1-oxopropyl]amino]-2-hydroxy-5-methylhexanoic acid, 1-methylethyl ester In a process analogous to Example 1 by substituting [2R-[2R*,3S*(S*)]]-2-hydroxy-5-methyl-3-[[2-[[2-(1-naphthalenylmethyl)-1,4-dioxo-4-phenylbutyl]amino]-1-oxo-3-[1-triphenylmethyl)-1H-imidazol-4-yl]propyl]amino]hexanoic acid, 1-methylethyl ester (European Patent 0,190,891) for N-[(1,1-dimethylethoxy)carbonyl]-L-phenylalanyl-N-[1-[1-hydroxy-2-(1-methylethoxy)-2-oxoethyl]-3-methylbutyl]-1-(triphenylmethyl)-L-histidinamide (mixture of [1S-[1R*(R*)]] and [1S-[1R*(S*)]]isomers) one obtains the title compound; mp 108°–118° C.

EXAMPLE 2

[2R-[2R*,3S*(S*)]]-2-hydroxy-5-methyl-3-[[6-[[(methylamino)thioxomethyl]amino]-2-[[3-(1-naphthalenyl)-2-(1-naphthalenylmethyl)-1-oxopropyl]amino]-1-oxohexyl]amino]hexanoicacid, 1-methylethyl ester

[2R-[2R*,3S*(S*)]]-3-[[6-amino-2-[[3-(1-naphthalenyl)-2-(1-naphthalenylmethyl)-1-oxopropyl]amino]-1-oxohexyl]amino]-2-hydroxy-5-methylhexanoic acid, 1-methylethyl ester (Example K), 3.44 g (5.3 mmol), is dissolved in 65 ml of chloroform, 0.42 g (5.7 mmol) of methyl isothiocyanate is added, and the reaction mixture is stirred at room temperature overnight under a nitrogen atmosphere. The reaction mixture is concentrated and 2.05 g (53% yield) of the title compound is obtained after flash chromatography over silica gel 60 (230–400 mesh) and elution with hexane-ethyl acetate (1:4); mp softens at 89° C., melts at 93°–95° C.

EXAMPLE 2a

[2R-[2R*,3S*(S*)]]-2-hydroxy-5-methyl-3-[[6-[[(methylamino)thioxomethyl]amino]-2-[[4-(4-morpholinyl)-2-1-naphthalenylmethyl)-1,4-dioxobutyl]amino]-1-oxohexyl]amino]hexanoic acid, 1-methylethyl ester In a process analogous to Example 2 by substituting [2R-[2R*,3S*(S*)]]-3-[[6-amino-2-[[4-[4-morpholinyl)-2-(1-naphthalenylmethyl)-1,4-dioxobutyl]amino]-1-oxohexyl]amino]2-hydroxy-5-methylhexanoic acid, 1-methylethyl ester (Example L) for [2R-[2R*,3S*(S*)]]-3-[[6-amino-2-[[3-(1-naphthalenyl)-2-(1-naphthalenylmethyl)-1-oxopropyl]amino-1-oxohexyl]amino]-2-hydroxy-5-methylhexanoic acid, 1-methylethyl ester one obtains the title compound; mp gels at 80° C., melts at 122° C.

EXAMPLE 2b

[2S-[2R*,3R*(R*)]]-2-hydroxy-5-methyl-3-[[6-[[(methylamino))thioxomethyl]amino]-2-[[4-(4-morpholinyl)-2-(1-naphtalenylmethyl)-1,4-dioxobutyl]amino]-1-oxohexyl]amino]hexanoic acid, 1-methylethyl ester In a process analogous to Example 2 by substituting [2S-[2R*,3R*(R*)]]-3-[[6-amino-2-[[4-(4-morpholinyl)-2-(1-naphthalenylmethyl)-1,4-dioxobutyl]amino]-1-oxohexyl]amino]-2-hydroxy-5-methylhexanoic acid, 1-methylethyl ester (Example M) for [2R-[2R*,3S*(S*)]]-3-[[6-amino-2-[[3-(1-naphthalenyl)-2-(1-naphthalenylmethyl)-1-oxopropyl]amino]-1-oxohexyl]amino]-2-hydroxy-5-methylhexanoic acid, 1-methylethyl ester one obtains the title compound; mp gels at 88° C., melts at 94°–96° C.

PREPARATIVE EXAMPLES FOR INTERMEDIATES

Example A

3-Amino-2-hydroxy-5-methylhexanoic acid (C3 is S; C2 is mixture of R,S)

To a suspension of (S)-(1-formyl-2-phenylethyl)carbamic acid, 1,1-dimethylethyl ester, 100.01 g (0.465 mol), and zinc iodide, 0.75 g, in chloroform (300 ml) is added, under a nitrogen atmosphere, trimethylsilylcyanide, 60.0 g, (0.604 mol). The solution is stirred at room temperature for 48 hours, evaporated in vacuo, the residue dissolved in dioxane (300 ml) treated with water (100 ml) concentrated hydrochloric acid (300 ml) and heated at reflux for 16 hours,. The solution is cooled to room temperature and the solvents evaporated in vacuo to give a tan solid. This is dissolved in water (200 ml) and applied to a Dowex 50×8 column. The column is washed with water until the wash is neutral and then eluted with 2N ammonia. The appropriate fractions are evaporated to dryness and the residue is triturated with acetone to give the title compound as a white solid, 26.5 g (35.3%); mp 245° C.(d).

Example B (3S)-3-Amino-2-hydroxy-5-methylhexanoic acid, 1-methylethyl ester, monohydrochloride (mixture of isomers at 2-hydroxy center)

3-Amino-2-hydroxy-5-methylhexanoic acid (Example A), 26.5 g (0.164 mol), is dissolved in isopropyl alcohol, treated with hydrochloric acid (anhydrous) for five minutes, treated with toluene (250 ml) and 3A molecular seives and warmed to reflux for 15 minutes. The solution is cooled to room temperature, filtered, and the solvents evaporated in vacuo to give the title compound as an extremely hygroscopic foam, 40 g. The foam is used without further purification.

Example C

[S-(R*,R*)]-3-[[(1,1-dimethylethoxy)carbonyl]amino]-2-hydroxy-5-methylhexanoic acid, 1-methylethyl ester (3S)-3-amino-2-hydroxy-5-methylhexanoic acid, 1-methylethyl ester, monohydrochloride (mixture of isomers at 2-hydroxy center) (Example B), 39.3 g (0.164 mmol) is added to a mixture of water (225 ml), dioxane (225 ml), and triethylamine, 40.4 g (0.4 mol), and treated over five minutes with di-tertiary-butyldicarbonate, 39.3 g (0.18 mol), [in five gram increments]. The mixture is stirred at room temperature overnight, diluted with water (700 ml) and extracted with ethyl acetate (2×350 ml). The combined organics are washed with saturated brine and dried over magnesium sulfate. The solvents are evaporated in vacuo to given an oil which is chromatographed on silica gel using ethyl acetate:-hexane (1:4). The fast running isomer (2R,3S) is isolated by evaporation of the appropriate fractions to give an oil, 28 g (57%). [α]$_D$= −25.4 (C=1.085, methanol). The slow running isomer (2S,3S) is isolated in the same manner to give an oil, 17 g (34%). [α]$_D$= −9.1 (C=0.45, methanol).

Example D

β-amino-α-hydroxybenzenebutanoic acid (mixture of [R-(R*,S*)] and [S-(R*,R*)] isomers)

(S)-(1-formyl-2-phenylethyl)carbamic acid, 1,1-dimethylethyl ester, 9.2 g (36.9 mmol), is stirred in chloroform (30 ml) treated with zinc iodide, 100 mg, and trimethylsilylcyanide, 6.4 g (47.9 mmol). The solution is stirred at room temperature overnight, evaporated in vacuo and dissolved in a mixture of dioxane (100 ml) and concentrated hydrochloric acid (100 ml) warmed to reflux and stirred for 24 hours. The solution is cooled to room temperature and evaporated free of dioxane. The aqueous solution is washed once with diethyl ether (125 ml) and evaporated to dryness. The residue is dissolved in 1N hydrochloric acid and applied to a Dowex 50×8 (H+) column (50 g). The column is flushed with water (300 ml) and the compound eluted with 2N ammonia water:acetonitrile (0–50% gradient, 600 ml). The appropriate fractions are evaporated in vacuo and the residue triturated with acetone (100 ml) to give 1.75 g (24%) of the title compound as a white solid; mp 239° C. (d).

Example E

β-[[(1,1-dimethylethoxy)carbonyl]amino]-α-hydroxybenzenebutanoic acid, 1-methylethyl ester (mixture of [R-(R*,S*)] and [S-(R*,R*)]isomers)

Hydrochloric acid gas is passed into a solution of β-amino-α-hydroxybenzenebutanoic acid (mixture of [R-(R*,S*)] and [S-(R*,R*)]) (Example D), 1.5 g (7.6 mmol), in 15 ml of isopropanol for ten minutes. To this is added toluene and 3A molecular seives, 10 g, and the solution warmed to reflux for 15 minutes. The mixture is filtered and evaporated in vacuo to give an extremely hygroscopic foam which is added to a solution of triethyl amine, 1.6 g (16 mmol), in water (15 ml) and dioxane (15 ml). To this is added di-tertiarybutyldicarbonate and the mixture is stirred at room temperature for 72 hours. The solution is diluted with water (175 ml) and extracted with ethyl acetate (2×75 ml). The organics are separated, dried over magnesium sulfate and the solvents evaporated in vacuo to give an oil. The oil is chromatographed (flash silica gel (200 g), 8:2, hexane:ethyl acetate, 15 ml fractions). The appropriate fractions are evaporated in vacuo to give 1.8 g (70%) of the title compound as an oil, which solidifies upon standing.

Example F

β-[[(1,1-dimethylethoxy)carbonyl]amino]-α-hydroxycyclohexanebutanoic acid, 1-methylethyl ester (mixture of [R-(R*,S*)] and [S-(R*,R*)]isomers)

To β-[[(1,1-dimethylethoxy)carbonyl]amino]-α-hydroxybenzenebutanoic acid, 1-methylethyl ester (mixture of R-(R*,S*)] and [S-(R*,R*)]isomers) (Example E), 4.2 g (12.4 mmol), in isopropanol (100 ml) is added 10% rhodium on carbon, 1.0 g, and the mixture is stirred under a hydrogen atmosphere for 16 hours. The solution is filtered and evaporated in vacuo to give a 3.6 g (85%) of the title compound as a tan oil.

Example G

β-amino-α-hydroxycyclohexanebutanoic acid, 1-methylethyl ester (mixture of [R-(R*,S*)] and [S-(R*,R*)]isomers)

β-[[(1,1-dimethylethoxy)carbonyl]amino]-α-hydroxycyclohexanebutanoic acid, 1-methylethyl ester (mixture of [R-(R*,S*)] and [S-(R*,R*)]isomers) (Example F), 3.4 g (10 mmol), is dissolved in methylene chloride, cooled to 0° C. and hydrochloric acid gas is bubbled in for five minutes every 15 minutes for two hours. The solution is diluted with ethyl acetate (50 ml) washed with saturated sodium bicarbonate solution (100 ml) and then with saturated brine solution (100 ml). The organics are separated, dried over magnesium sulfate and evaporated to dryness in vacuo to give 1.75 g (73%) of the title compound as an oil.

Example H

N-[(1,1-dimethylethoxy)carbonyl]-L-phenylalanyl-N-[1-[1-hydroxy-2-(1-methylethoxy)-2-oxoethyl]-3-methylbutyl]-1-(triphenylmethyl)-L-histidinamide (mixture of [S-(R*,R*)] and [R-(R*,S*)]isomers)

Step A: Preparation of 2-hydroxy-5-methyl-3-[[1-oxo-2[[(phenylmethoxy)carbonyl]amino]-3-[1-(triphenylmethyl)-1H-imidazol-4-yl]propyl]amino]hexanoic acid (mixture of [2R-[2R*,3S*(S*)]] and [2S-[2R*,3R*(R*)]]isomers)

A mixture of 12.4 g (23.4 mmol) of N-[(phenylmethoxy)carbonyl]-1-(triphenylmethyl)-L-histidine, (Jones, J. H., et al, Synthesis, page 1110 (1987)) 3.3 g (24.6 mmol) of 1-hydroxybenzotriazole and 50 ml of dimethylformamide is cooled to <0° C. and treated with a mixture of 5.6 g (23.4 mmol) of (3S)-3-amino-2-hydroxy-5methylhexanoic acid, 1-methylethyl ester, monohydrochloride (mixture of isomers at hydroxy center) (Example B), and 2.5 g (25 mmol) of triethylamine in 30 ml of dimethylformamide at −5° C. The solution is stirred for five minutes, treated with 5.1 g (24.6 mmol) of dicyclohexylcarbodiimide in 30 ml of dimethylformamide and stirred for eight hours at −5 to 0° C., kept at −5° C. overnight, allowed to warm to room temperature under a nitrogen atmosphere and stirred for 24 hours. The mixture is treated with 1 g (10 mmol) of triethylamine, stirred at room temperature for 72 hours, filtered and the dimethylformamide evaporated in vacuo. The residue is dissolved in 200 ml of ethyl acetate, extracted with 200 ml of 1N citric acid solution, filtered, extracted with 200 ml of saturated sodium chloride solution, 200 ml of saturated solution of sodium bicarbonate and 200 ml of saturated solution of sodium chloride. The organic layer is separated, dried (magnesium sulfate) and the solvent evaporated in vacuo to give 14.1 g of the title compound as a tan foam.

Step B: Preparation of 3-[[2-amino-1-oxo-3-[1-(triphenylmethyl)-1H-imidazol-4-yl]propyl]amino]-2-hydroxy-5-methylhexanoic acid, 1-methylethyl ester (mixture of [2R-[2R*,3S*(S*)]] and [2S-[2R*,3R*(R*)]]-isomers)

Palladium on charcoal, 10%, 1 g, is added to 11.8 g (16.5 mmol) of 2-hydroxy-5-methyl-3-[[1-oxo-2[[(phenylmethoxy)carbonyl]amino]-3-[1-(triphenylmethyl)-1H-imidazol-4-yl]propyl]amino]hexanoic acid (mixture of [2R-[2R*,3S*(S*)]] and [2S-[2R*,3R*(R*)]]isomers) dissolved in isopropanol and the mixture is exposed to hydrogen gas. After complete uptake of hydrogen the mixture is filtered, the solvent evaporated in vacuo and the residue co-evaporated with diethyl ether to give 9.5 g of the title compound as a beige foam after drying under high vacuum for one hour.

Step C: Preparation of N-[(1,1-dimethylethoxy)carbonyl]-L-phenylalanyl-N-[1-[1-hydroxy-2-(1-methylethoxy)-2-oxoethyl]-3-methylbutyl]-1-(triphenylmethyl)-L-histidinamide (mixture of [S-[R*,R*)]] and [R-(R*,S*)]isomers)

To a mixture of 1.1 g (4 mmol) of N-[(1,1dimethylethoxy)carbonyl]-L-phenylalanine and 0.568 g (4.2 mmol) of 1-hydroxybenzotriazole in 5 ml of dimethylformamide at 0° C. is added 2.4 g (4.1 mmol) of 3-[[2-amino-1-oxo-3-[1-(triphenylmethyl)-1H-imidazol-4-yl]propyl]amino]-2-hydroxy-5-methylhexanoic acid, 1-methylethyl ester (mixture of [2R-[2R*,3S*(S*)]] and [2S-[2R*,3R*(R*)]]-isomers) in 15 ml of dimethylformamide. The solution is stirred for five minutes, treated with 0.867 g (4.2 mmol) of dicyclohexylcarbodiimide, stirred at 0° C. for one hour, warmed to room temperature, stirred overnight, filtered and the dimethylformamide evaporated in vacuo. The resulting oil is dissolved in ethyl acetate and washed successively with 30 ml of 1N citric acid solution, 30 ml of saturated solution of sodium bicarbonate and 30 ml of saturated solution of sodium chloride. The organic layer is separated, dried (magnesium sulfate) and evaporated in vacuo to a foam. The foam is chromatographed over 250 g of silica gel (230–400 mesh), eluted with 5% methanol 95% chloroform, the combined fractions evaporated in vacuo and the residue dried under high vacuum overnight to afford 2.3 g of the title compound as a white foam.

EXAMPLE I

2-Hydroxy-5-methyl-3-[[2-[[3-(1-naphthalenyl)-2(1-naphthalenylmethyl)-3-oxopropyl]amino]-1-oxo-3-[1-(triphenylmethyl)-1H-imidazol-4-yl]propyl]amino]hexanoic acid, 1-methylethyl ester (mixture of [2R-[2R*,3S*(S*)]] and [2S-[2R*,3R*(R*)]-isomers)

In a process analogous to Example H by substituting α-(1-naphthalenylmethyl)-1-naphthalenepropanoic acid for N-[(1,1-dimethylethoxy)carbonyl]-L-phenylalanine (see Example H, Step C) one obtained the title compound as a light yellow foam.

Example J

[2R-[2R*,3S*(S*)]]-2-hydroxy-5-methyl-3-[[2-[[3-(1-naphthalenyl)-2-(1-naphthalenylmethyl)-3-oxopropyl]amino]-1-oxo-3-[1-(triphenylmethyl)-1H-imidazol-4-yl]propyl]amino]hexanoic acid, 1-methylethyl ester In a process analogous to Example H by substituting α-(1-naphthalenylmethyl)-1-naphthalenepropanoic acid for N-[(1,1-dimethylethoxy)carbonyl]-L-phenylalanine and [2R-[2R*,3S*(S*)9 ]-3-[[2-amino-1-oxo-3-[1-(triphenylmethyl)- 1H-imidazol-4-yl]propyl]amino]-2-hydroxy-5-methylhaxanoic acid, 1-methylethyl ester for 3-[[2-amino-1-oxo-3-[1-(triphenylmethyl)-1H-imidazol-4-yl]propyl]amino]-2-hydroxy-5-methylhexanoic acid, 1-methylethyl ester (mixture of [2R-[2R*,3S*(S*)]] and [2S-[2R*,3R*(R*)]]-isomers) (see Example H, Step C) one obtains the title compound as a white foam.

Example K

[2R-[2R*,3S*(S*)]]-3-[[6-amino-2-[[3-(1-naphthalenyl)-2-(1-naphthalenylmethyl)-1-oxopropyl]amino]-1-oxohexyl]amino]-2-hydroxy-5-methylhexanoic acid, 1-methylethyl ester Step A: Preparation of
N-[3-(1-Naphthalenyl)-2-(1-naphthalenylmethyl)-1-oxopropyl]-N6-[(phenylmethoxy)carbonyl]-L-lysine In process analogous to Example H by substituting α-(1-naphthalenylmethyl)-1-naphthalenepropanoic acid (obtained by reacating di-tertiary-butylmalonate (one equivalent) with 1-chloromethylnaphthylene (two equivalents) and sodium hydride (two equivalents) followed by refluxing in acetic acid) for N-[(phenylmethoxy)carbonyl]-1-(triphenylmethyl)-L-histidine and Nε-carbobenzoxy-lysine, methyl ester for (3S)-3-amino-2-hydroxy-5-methylhexanoic acid, 1-methylethyl ester, monohydrochloride (mixture of isomers at hydroxy center) one obtains the methyl ester of the title compound which is then hydrolyzed with sodium hydroxide in aqueous methanol to afford the title compound.

Step B: Preparation of
[2R-[2R*,3S*(S*)]]-2-hydroxy-5-methyl-3-[[2-[[3-(1-naphthalenyl)-2-(1-naphthalenylmethyl)-1-oxopropyl]amino]-1-oxo-6-[[(phenylmethoxy)carbonyl]amino]-hexyl]amino]hexanoic acid, 1-methylethyl ester N-[3-(1-naphthalenyl)-2-(1-naphthalenylmethyl)-1-oxopropyl]-N6-[(phenylmethoxy)carbonyl]-L-lysine, 4 g (6.6 mmol), 1.58 g (6.6 mmol) of [2R-(2R*,3S*)]-3-amino-2-hydroxy-5-methylhexanoic acid, 1-methylethyl ester, monohydrochloride, and 1.79 g (13.2 mmol) of 1-hydroxybenzotriazole are combined in 80 ml of dimethylformamide. The [2R-(2R*,3S*)]-3-amino-2-hydroxy-5-methylhexanoic acid, 1-methylethyl ester, monohydrochloride is neutralized with 1.4 ml (10.1 mmol) of triethylamine. The solution is cooled to −10° C. and 1.36 g (6.6 mmol) of dicyclohexylcarbodiimide is added with stirring. The reaction mixture is kept cold for 8 hours while stirring under nitrogen, allowed to warm to room temperature overnight, filtered, the filtrate concentrated and the residue partitioned between ethyl acetate and water. The organic layer is separated and extracted with saturated solution of sodium bicarbonate, dried (sodium sulfate), filtered and concentrated. The residue is flash chromatographed over silica gel 60 (230–400 mesh), eluted with hexane-ethyl acetate (2:3), the eluates collected, dissolved in diethyl ether, filtered and the filtrate concentrated to afford 4.01 g (77%) of the title compound as a white amorphous solid.

Step C: Preparation of
[2R-[2R*,3S*(S*)]]-3-[[6-amino-2-[[3-(1-naphthalenyl)-2-(1-naphthalenylmethyl)-1-oxopropyl]amino]-1-oxohexyl]amino]-2-hydroxy-5-methylhexanoic acid, 1-methylethyl ester

[2R-[2R*,3S*(S*)]]-2-hydroxy-5-methyl-3-[[2-[[3-(1-naphthalenyl)-2-(1-naphthalenylmethyl)-1-oxopropyl]amino]-1-oxo-6-[[(phenylmethoxy)carbonyl]amino]-hexyl]amino]hexanoic acid, 1-methylethyl ester, 3.97 g (5.0 mmol), is dissolved in 250 ml of absolute ethanol, 0.5 g of 20% palladiun charcoal is added, and the mixture exposed to hydrogen gas for 18 hours. After complete uptake of hydrogen the mixture is filtered and concentrated to afford 3.44 g of the title compound.

Example L

[2R-[2R*,3S*(S*)]]-3-[[6-amino-2-[[4-(4-morpholinyl)-2-(1-naphththalenylmethyl)-1,4-dioxobutyl]amino]-1-oxohexyl]amino]-2-hydroxy-5-methylhexanoic acid, 1-methylethyl ester In a process analogous to Example K by substituting N-[4-(4-morpholinyl)-2-(1-naphthalenylmethyl)-1,4-dioxobutyl]-N6-[(phenylmethoxy)carbonyl]-L-lysine (obtained by dicylohexylcarbodiimide coupling of α-(1-naphthalenylmethyl)-γ-oxo-4-morpholinebutanoic acid (European Patent Application 0,200,406) and N6-[(phenylmethoxy)carbonyl-L-lysine, methyl ester followed by hydrolysis of the resulting ester) for N-[3-(1-naphthalenyl)-2-(1-naphthalenylmethyl)-1-oxopropyl]-N6-[(phenylmethoxy)carbonyl]-L-lysine one obtains the title compound as an off-white foam.

Example M

[2R*,3R*(R*)]]-3-[[6-amino-2-[[4-(4-morpholinyl)-2-(1-naphthalenylmethyl)-1,4-dioxobutyl]amino]-1-oxohexyl]amino-2-hydroxy-5-methylhexanoic acid,1-methylethyl ester In a process analogous to Example K by substituting N-[4-(4-morpholinyl)-2-(1-naphthalenylmethyl)-1,4-dioxobutyl]-N⁶-[(phenylmethoxy)carbonyl]-L-lysine for N-[3-(1-naphthalenyl)-2-(1naphthalenylmethyl)-1-oxopropyl]-N⁶-[(phenylmethoxy)carbonyl]-L-lysine and [2S-[2R*,3R*)]-3amino-2-hydroxy-5-methylhexanoic acid, 1-methylethyl ester, monohydrochloride for [2R-(2R*,3S*)]-3-amino-2-hydroxy-5-methylhexanoic acid, 1-methylethyl ester, monohydrochloride one obtains the title compound as a white foam.

We claim:

1. A compound having the formula I

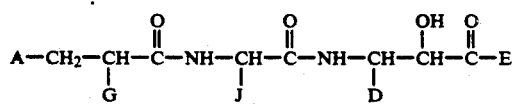

or a pharmaceutically acceptable acid addition salt thereof, wherein A is naphthyl, phenyl, or phenyl substituted with alkyl of from one to four carbon atoms, or alkoxy of from one to four carbon atoms; G is naphthylmethyl,

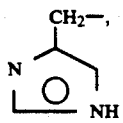

D is

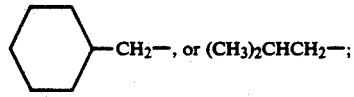

and E is $R_5O-$, wherein $R_5$ is alkyl of from one to five carbon atoms.

2. A compound as defined in claim 1 wherein A is 1-naphthyl, phenyl, or 4-methoxyphenyl; G is 1-naphthylmethyl;

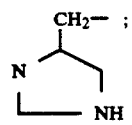

D is

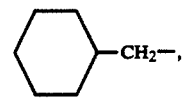

or $(CH_3)_2CHCH_2$; and E is $R_5O-$, wherein $R_5$ is alkyl of from one to five carbon atoms.

3. A compound as defined in claim 2 wherein G is 1-naphthylmethyl; J is

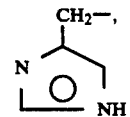

4. A compound as defined in claim 3 selected from the group consisting of 2-hydroxy-3[[3-(1H-imidazol-4-yl)-2-[[3-(1-naphthalenyl)-2-(1-naphthalenylmethyl)-1-oxopropyl]amino]-1-oxopropyl]amino]-5-methylhexanoic acid, 1-methylethyl ester, acetate (1:1) (salt) (hydroxy center is RS; all other centers are S); [2R-[2R*,3S*(S*)]]-2-hydroxy-3-[[3-(1H-imidazol-4-yl)-2-[[3-(1-napthhalenyl)-2-(1-naphthalenylmethyl)-1-oxopropyl]amino]-1-oxopropyl] amino]-5-methylhexanoic acid, 1-methylethyl ester.

5. A pharmaceutical composition comprising a renininhibitory effective amount of a compound as claimed in claim 1 in combination with a pharmaceutically acceptable carrier.

6. A method of treating renin-associated hypertension which comprises administering to a mammal a pharmaceutical composition as claimed in claim 5.

* * * * *

UNITED STATES PATENT AND TRADEMARK OFFICE
CERTIFICATE OF CORRECTION

PATENT NO. : 5,135,914
DATED : August 4, 1992
INVENTOR(S) : H.W. Hamilton and W.C. Patt It is certified that error appears in the above-indentified patent and that said Letters Patent is hereby corrected as shown below:

Column 25, line 30, delete "," and insert —; J is—;
line 37, insert —;—before D.

Column 26, line 34, insert —and— after ;.

Signed and Sealed this

Twelfth Day of October, 1993

BRUCE LEHMAN

*Attest:*

*Attesting Officer*    *Commissioner of Patents and Trademarks*

UNITED STATES PATENT AND TRADEMARK OFFICE
CERTIFICATE OF CORRECTION

PATENT NO. : 5,135,914
DATED : August 4, 1992
INVENTOR(S) : H.W. Hamilton and W.C. Patt It is certified that error appears in the above-indentified patent and that said Letters Patent is hereby corrected as shown below:

At column 26, lines 3-10 delete "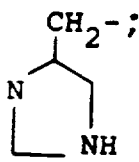"     insert --          -- after ";" on line 3 and before "D" on line 11.

Signed and Sealed this

Twenty-second Day of March, 1994

Attest:

BRUCE LEHMAN

Attesting Officer    Commissioner of Patents and Trademarks